(12) United States Patent
Iyer et al.

(10) Patent No.: US 7,725,190 B2
(45) Date of Patent: May 25, 2010

(54) IMPLANTABLE MEDICAL DEVICE FEEDTHROUGH ASSEMBLY INCLUDING FLANGE PLATE

(75) Inventors: Rajesh V. Iyer, Eden Prairie, MN (US); Shawn D. Knowles, Saint Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 267 days.

(21) Appl. No.: 11/343,056

(22) Filed: Jan. 30, 2006

(65) Prior Publication Data

US 2007/0179553 A1    Aug. 2, 2007

(51) Int. Cl.
*A61N 1/375* (2006.01)
(52) U.S. Cl. ........................................ 607/36
(58) Field of Classification Search .............. 607/36–38
See application file for complete search history.

(56) References Cited

U.S. PATENT DOCUMENTS

| | | | | |
|---|---|---|---|---|
| 5,333,095 | A | * | 7/1994 | Stevenson et al. ........... 361/302 |
| 5,336,246 | A | * | 8/1994 | Dantanarayana ............. 607/37 |
| 5,870,272 | A | | 2/1999 | Seifried et al. |
| 6,414,835 | B1 | | 7/2002 | Wolf et al. |
| 6,566,978 | B2 | | 5/2003 | Stevenson et al. |
| 6,574,508 | B2 | * | 6/2003 | Zaouali et al. ................. 607/36 |
| 6,768,629 | B1 | * | 7/2004 | Allen et al. .................. 361/302 |
| 6,855,456 | B2 | | 2/2005 | Taylor et al. |
| 2007/0043399 | A1 | * | 2/2007 | Stevenson et al. ............. 607/37 |

* cited by examiner

*Primary Examiner*—Scott M Getzow
*Assistant Examiner*—Amanda Patton

(57) ABSTRACT

A medical device feedthrough assembly includes a flange plate formed with a plurality of receptacles. A feedthrough subassembly is mounted within each of the receptacles, and a ferrule of each subassembly is coupled to the flange plate.

24 Claims, 7 Drawing Sheets

IMPLANTABLE MEDICAL DEVICE FEEDTHROUGH ASSEMBLY INCLUDING FLANGE PLATE

FIELD OF THE INVENTION

The present invention pertains to implantable medical devices and more particularly to feedthrough assemblies thereof.

BACKGROUND OF THE INVENTION

Implantable medical devices (IMD's) including electronic circuitry and battery elements require a housing to contain and hermetically seal these elements within a body of a patient. Many of these IMD's include electrical feedthroughs to provide electrical connection between the elements contained within the housing and components of the IMD external to the housing, for example sensors and/or electrodes mounted on an exterior surface or electrical contacts housed in a connector module, which is mounted on the housing to provide coupling for medical electrical leads.

Feedthrough assemblies typically include a ferrule, which is coupled to a sidewall of the IMD housing, and a conductive pin extending through an insulator that is mounted within the ferrule. The insulator electrically isolates the pin from the ferrule and is sealed to the ferrule and the pin. Some feedthrough assemblies further include a capacitive element to provide high frequency filtering for the pin.

Many IMD's require a plurality of feedthroughs, and, in some cases, one of more of the plurality of feedthroughs are subject to performance requirements that differ from the rest of the feedthroughs. Thus, there is a need for feedthrough assembly components and methods that facilitate the incorporation of a plurality of feedthroughs.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION OF THE ILLUSTRATED EMBODIMENTS

The following detailed description is exemplary in nature and is not intended to limit the scope, applicability, or configuration of the invention in any way. Rather, the following description provides practical illustrations for implementing exemplary embodiments of the present invention.

Figure 1A:
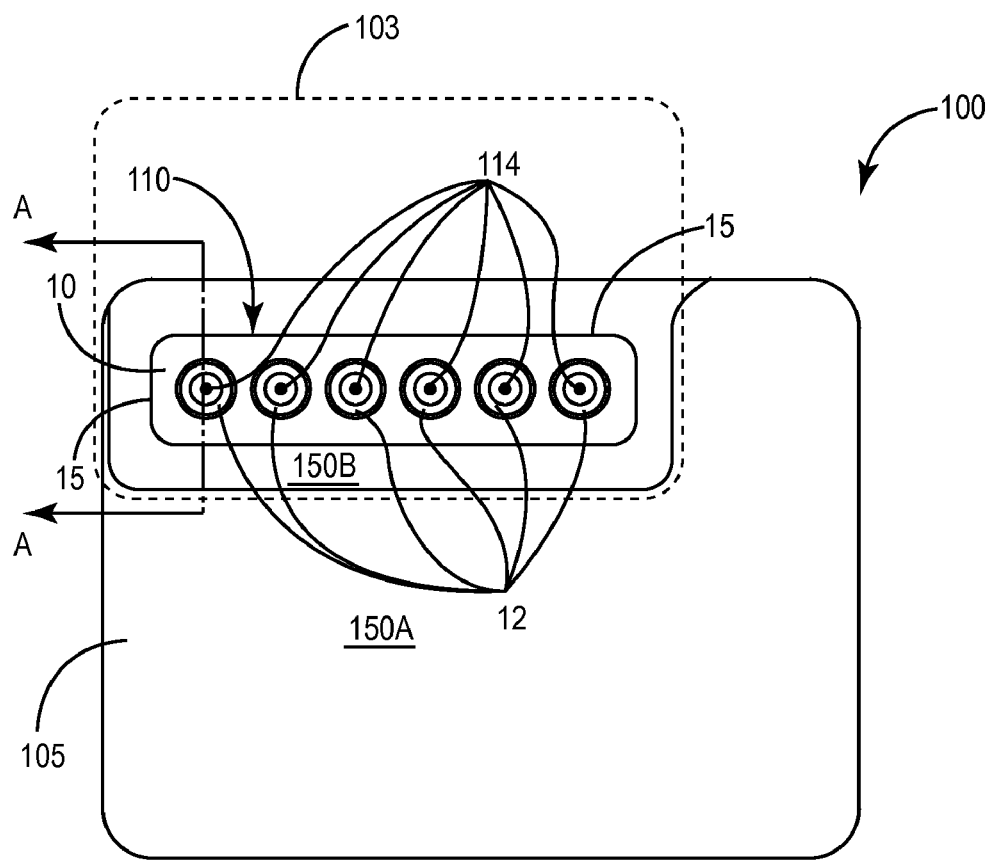
FIG. 1A is a plan view of a portion of an exemplary IMD including a feedthrough assembly, according to some embodiments of the present invention.

FIG. 1A is a plan view of a portion of an exemplary IMD including a feedthrough assembly 110, according to some embodiments of the present invention. FIG. 1A illustrates IMD 100 including a housing 105, feedthrough assembly 110 coupled to a recessed portion 150B of a sidewall 150A of housing 105, and a connector module 103 (shown by dashed lines) attached to housing 105 and overlaying feedthrough assembly 110. Feedthrough assembly 110 is shown to include a flange plate 10, being metallic or otherwise conductive, in which a plurality of feedthrough subassemblies, each including a ferrule 12 and a feedthrough pin 14, are mounted. According to the illustrated embodiment, connector module 103 may accommodate up to six electrical connections, between contacts, disposed therein, and feedthrough pins 14, which couple the contacts to electronic components, contained within housing 105. It should be noted, however, that embodiments of the present invention are not limited by a particular number of connections. Those skilled in the art will appreciate that module 103 may include one or more bores to facilitate connection of one or more medical electrical lead connectors to the contacts disposed therein; connector module design and construction details are well known to those skilled in the art of IMD's.

Figure 1B:
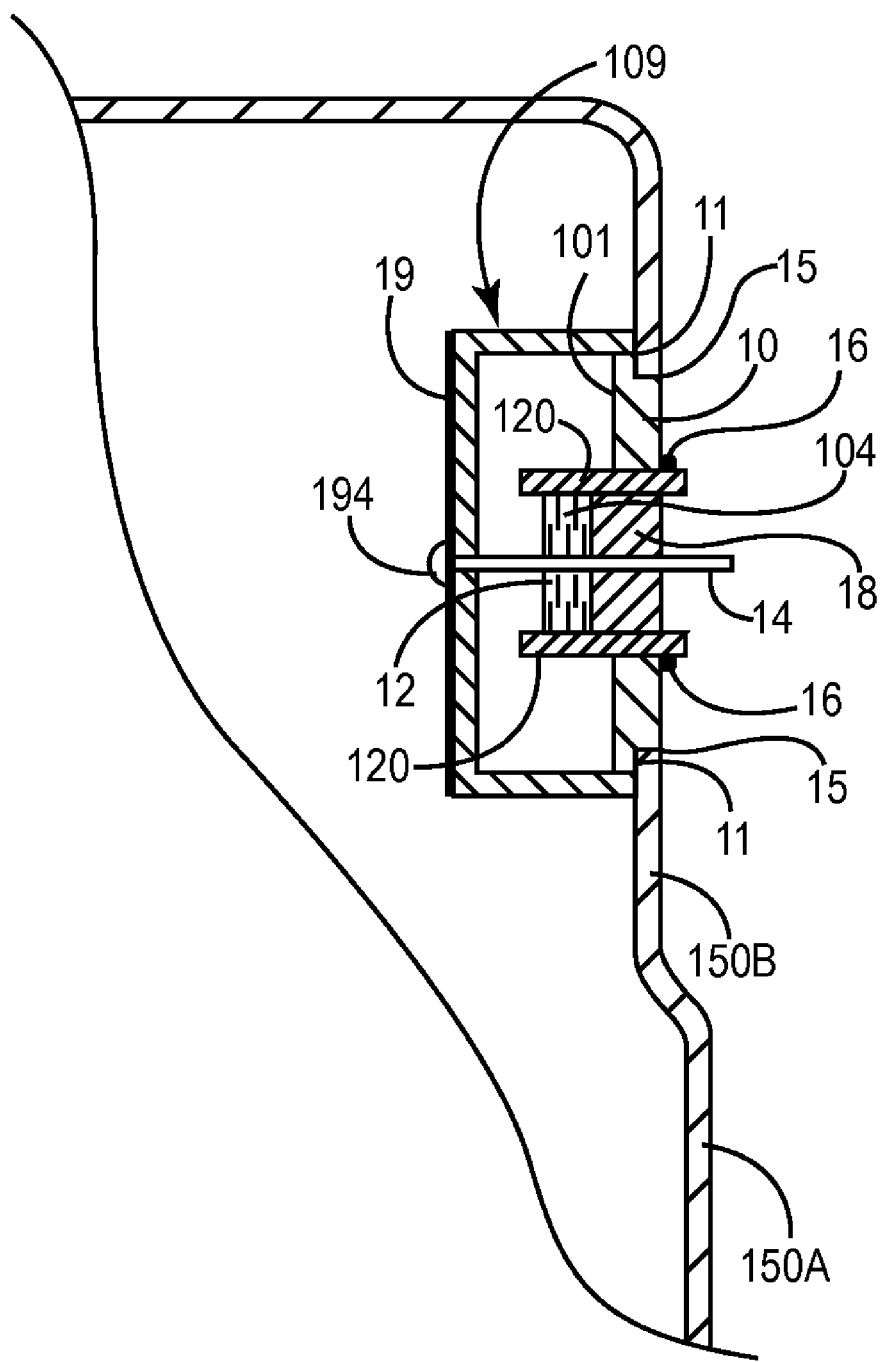
FIG. 1B is a section view through section line A-A of FIG. 1A.
Figure 1C:
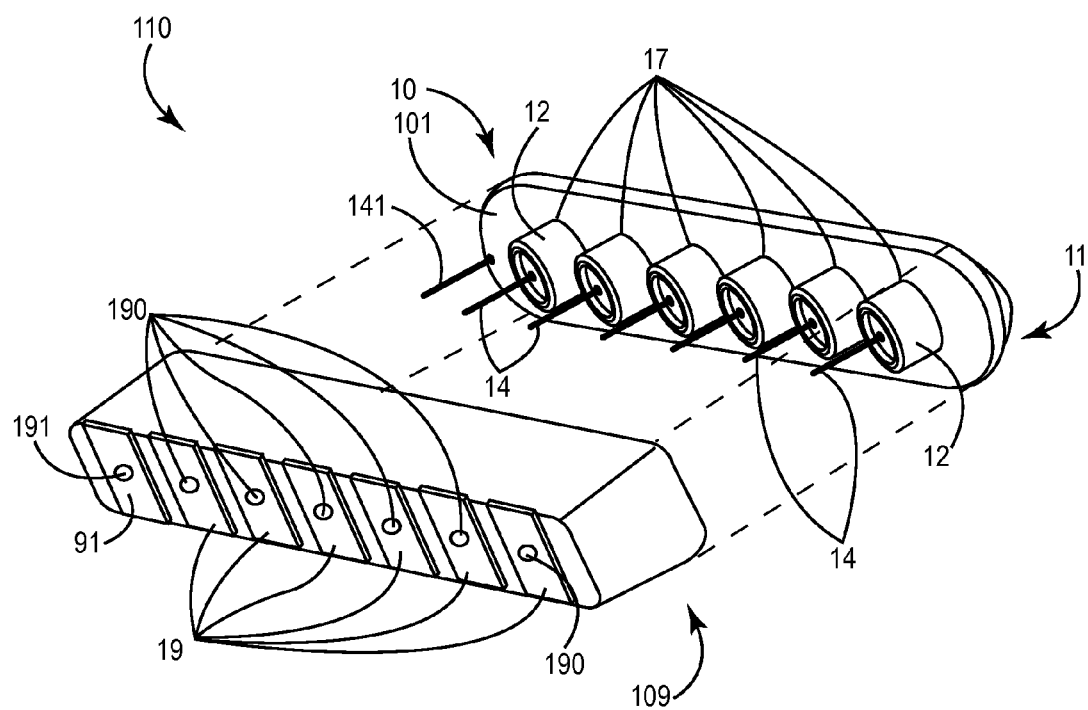
FIG. 1C is an exploded perspective view of the feedthrough assembly of FIG. 1, according to some embodiments of the present invention.

FIG. 1B is a partial section view through section line A-A of FIG. 1A; and FIG. 1C is an exploded perspective view of feedthrough assembly 110. FIGS. 1A-B illustrate flange plate 10 of feedthrough assembly 110 mounted within an opening of side wall portion 150B and coupled thereto, for example via welding, about a perimeter 15 of flange plate 10. According to the illustrated embodiment, flange plate 10 includes a ledge 11 extending about perimeter 15 and butting up against an inner surface of side wall portion 150B. FIG. 1C illustrates flange plate 10 further including a plurality of receptacles, formed by holes 17 extending through flange plate 10, each of which hold a corresponding feedthrough subassembly that includes, inter alia, ferrule 12 and pin 14; each ferrule 12 of each subassembly is shown extending through corresponding hole 17. FIG. 1B illustrates ferrule 12, representative of each ferrule 12 of the plurality shown in FIGS. 1A and 1C, coupled to flange plate 10 via a weld joint 16 between a shoulder 120 of ferrule 12 and flange plate 10 where shoulder 17 extends over a perimeter of hole 17. According to certain embodiments, housing sidewall 150A, B, flange plate 10 and ferrules 12 are each formed from titanium or a titanium alloy and welded to one another according to methods, for example laser welding, known to those skilled in the art. Other suitable materials for ferrules 12 include, but are not limited to, niobium, molybdenum, tantalum, stainless steel, and alloys thereof.

FIGS. 1B-C further illustrate feedthrough assembly 110 including a plurality of electrically conductive contact pads 19, corresponding to feedthrough pins 14, mounted on an electronics module assembly (EMA) 109; each contact pad 19 includes an aperture 190 through which the corresponding pin 14 extends for coupling 194, for example by brazing, welding or with a conductive adhesive. Suitable materials for pins 14 are well known to those skilled in the art, and include, but are not limited to, niobium, titanium, molybdenum and tantalum. EMA 109 may be molded from a thermoplastic material, for example polysulfone or polypropylene. EMA 109 provides one way to electrically couple each feedthrough pin 14 to internal circuitry of IMD 100, via corresponding contact pads 19. FIG. 1C further shows a grounding pin 141, either integral with plate 10 or coupled thereto, for example by welding, protruding from a lower side 101 of flange plate 10, being aligned for extension through an aperture 191 of a conductive pad 91 of EMA 109, for coupling thereto, in a manner similar to the coupling of pins 14 to pads 19.

FIG. 1B further illustrates the feedthrough subassembly, representative of each subassembly of assembly 110, including an insulator 18, which is mounted within ferrule, surrounding feedthrough pin 14 to isolate pin 14 from ferrule, and a discoidal capacitor 104, known to those skilled in the art for high frequency filtering of pin 14, mounted between ferrule 12 and pin 14. According to embodiments of the present invention, insulator 18 is formed from any suitable electrically insulative ceramic-containing material, examples of which include alumina, such as sapphire, zirconium oxide, and Cabal-12 glass. According to some embodiments, insulator 18, for example formed of alumina or zirconium oxide, is sealed to ferrule 12 and pin 14 by a gold, platinum, silver or a copper-silver alloy, braze; methods for brazing feedthroughs are well known to those skilled in the art. According to other embodiments, insulator 18, for example formed from Cabal-12 glass, is sealed directly to ferrule 12 and pin 14 by a heating process, for example as described in commonly assigned U.S. Pat. No. 6,855,456, relevant parts of which are hereby incorporated by reference.

Figure 2A:
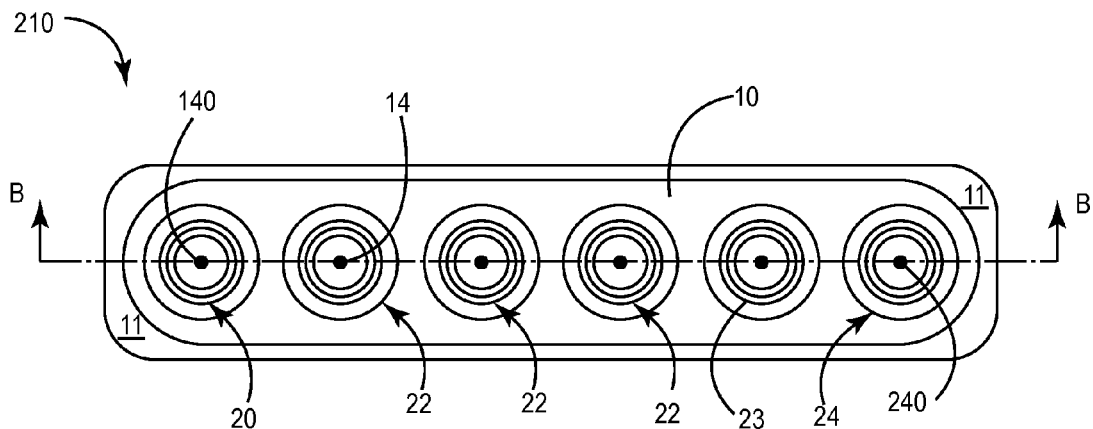
FIG. 2A is a top plan view of a feedthrough assembly according to additional embodiments of the present invention.
Figure 2B:
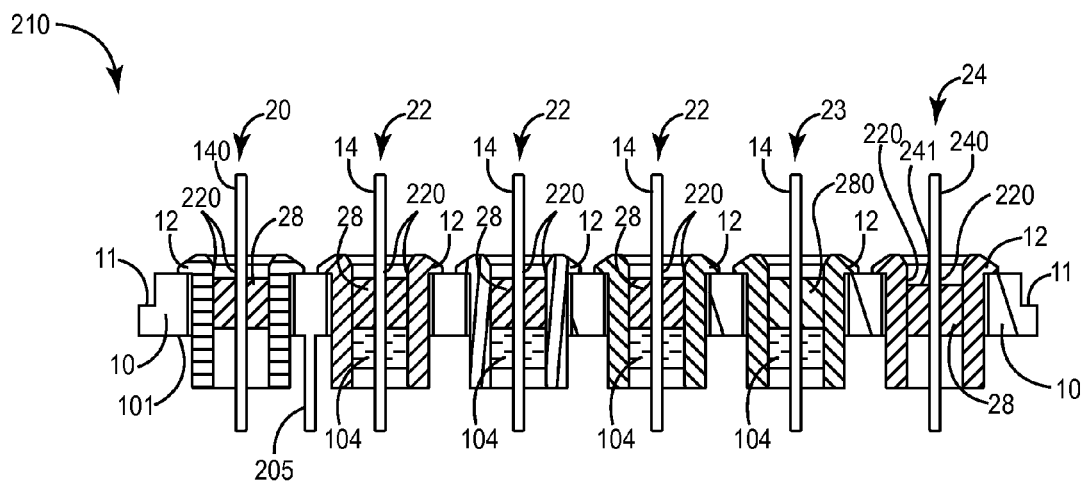
FIG. 2B is a section view through section line B-B of FIG. 2A.
Figure 2C:
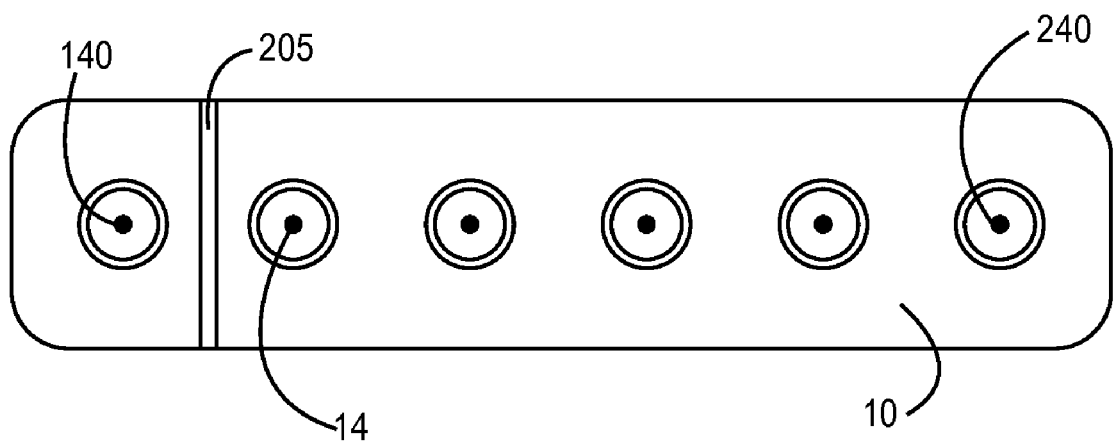
FIG. 2C is bottom plan view of the assembly of FIG. 2A.

FIGS. 2A and 2C are a top plan view and bottom plan view, respectively of a feedthrough assembly 210 according to additional embodiments of the present invention; and FIG. 2B is a section view through section line B-B of FIG. 2A. According to the illustrated embodiment, feedthrough subassemblies 20, 22, 23 and 24, mounted in flange plate 10, are of different designs. An insulator 280 of subassembly 23 differs from an insulator 28 in each of subassemblies 20, 22 and 24; and each of subassemblies 22 and 23 include high frequency filtering, via a discoidal capacitor 104, while subassemblies 20 and 24 do not include high frequency filtering.

FIG. 2B shows insulator 28 of each of subassemblies 20, 22 and 24 sealed to ferrule 12 and respective pins 140, 14 and 240 by a braze 220, as previously described, while insulator 280 of subassembly 23, being formed of a glass, for example Cabal-12 glass, is shown directly sealed to ferrule 12 and pin 14, as previously described. Such a glass seal may be less susceptible to corrosion than a brazed seal, and is particularly useful for a feedthrough that must accommodate voltage biases.

FIG. 2B further shows subassembly 20 including an antenna pin 140, and subassembly 24 including a grounding pin 240, neither of which require high-frequency filtering as do feedthrough pins 14 of subassemblies 22 and 23. With reference to subassembly 20, antenna pin 140, which would be coupled to an antenna (not shown) disposed outside an IMD housing, for example in connector module 103 of IMD 100 shown in FIG. 1, conducts high frequency signals, for example radio-frequency signals received and transmitted to and from the antenna during telemetry sessions. With reference to subassembly 24, grounding pin 240 is shown shorted to ferrule 12 via an 'overflow' of braze material 241 extending between pin 240 and ferrule 12; alternately, a conductive adhesive could be applied over insulator 28 shorting pin 240 to ferrule 12. Pin 240 may be coupled to an EMA in a manner similar to that described in conjunction with FIG. 1C.

FIGS. 2B-C further illustrate a wall 205, metallic or otherwise conductive, either formed integrally with plate 10 or coupled thereto, for example by welding, protruding from lower side 101 of plate 10 between antenna pin 140 and adjacent filtered pin 14, to shield filtered pins 14 against high frequency interference from pin 140. Wall 205 may extend over a length sufficient to span a gap between flange plate 10 and internal couplings of pins 140, 14, 240, for example to conductive pads of an EMA, such as EMA 109 shown in FIG. 1C.

Figure 3A:
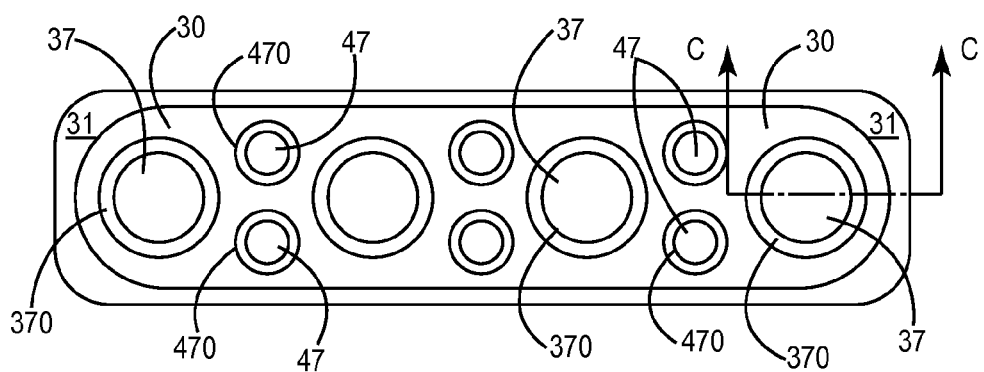
FIG. 3A is a top plan view of a flange plate for a feedthrough assembly according to some alternate embodiments of the present invention.
Figure 3B:
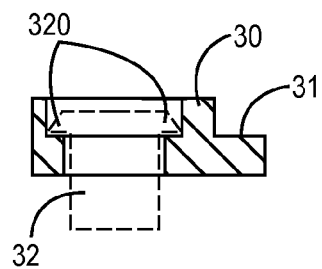
FIG. 3B is a section view through section line C-C of FIG. 3A.

FIG. 3A is a top plan view of a flange plate 30 for a feedthrough assembly according to some alternate embodiments of the present invention; and FIG. 3B is a section view through section line C-C of FIG. 3A. FIGS. 3A-B illustrates each receptacle including a hole 37, 47 and a counterbore 370, 470, which provides a recess for a coupling between flange plate 30 and each ferrule of corresponding feedthrough subassemblies, for example ferrule 32 shown with dashed lines in FIG. 3B. FIG. 3B illustrates a shoulder 320 of ferrule 32 extending laterally within counterbore 370 where it may be welded to flange plate. FIGS. 3A-B further illustrate flange plate 30 including a ledge 31 extending about a perimeter thereof, similar to ledge 11 of plate 10, which would be disposed within a sidewall of a housing when assembled in a device as part of a feedthrough assembly.

A feedthrough assembly including flange plate 30 is another example of how a feedthrough assembly can include feedthrough subassemblies of different designs. FIG. 3A illustrates plate 30 including a first plurality of receptacles, which are each formed by a hole 37 and a corresponding counterbore 370, and a second plurality of receptacles, which are each formed by a hole 47 and a corresponding counterbore 470. It can be seen that each hole 37 has a greater diameter than that of each hole 47 in order to accommodate a larger diameter feedthrough subassembly. In example, a feedthrough subassembly for high voltage applications would require a larger diameter insulator to isolate the feedthrough pin than would a subassembly designed for low voltage applications.

It may be appreciated that embodiments of the present invention, for example including flange plate 10 or flange plate 30, facilitate inclusion of more than one type of feedthrough in an IMD, each type being embodied by a different feedthrough subassembly that is manufactured according to different design and/or performance requirements.

Figure 4:
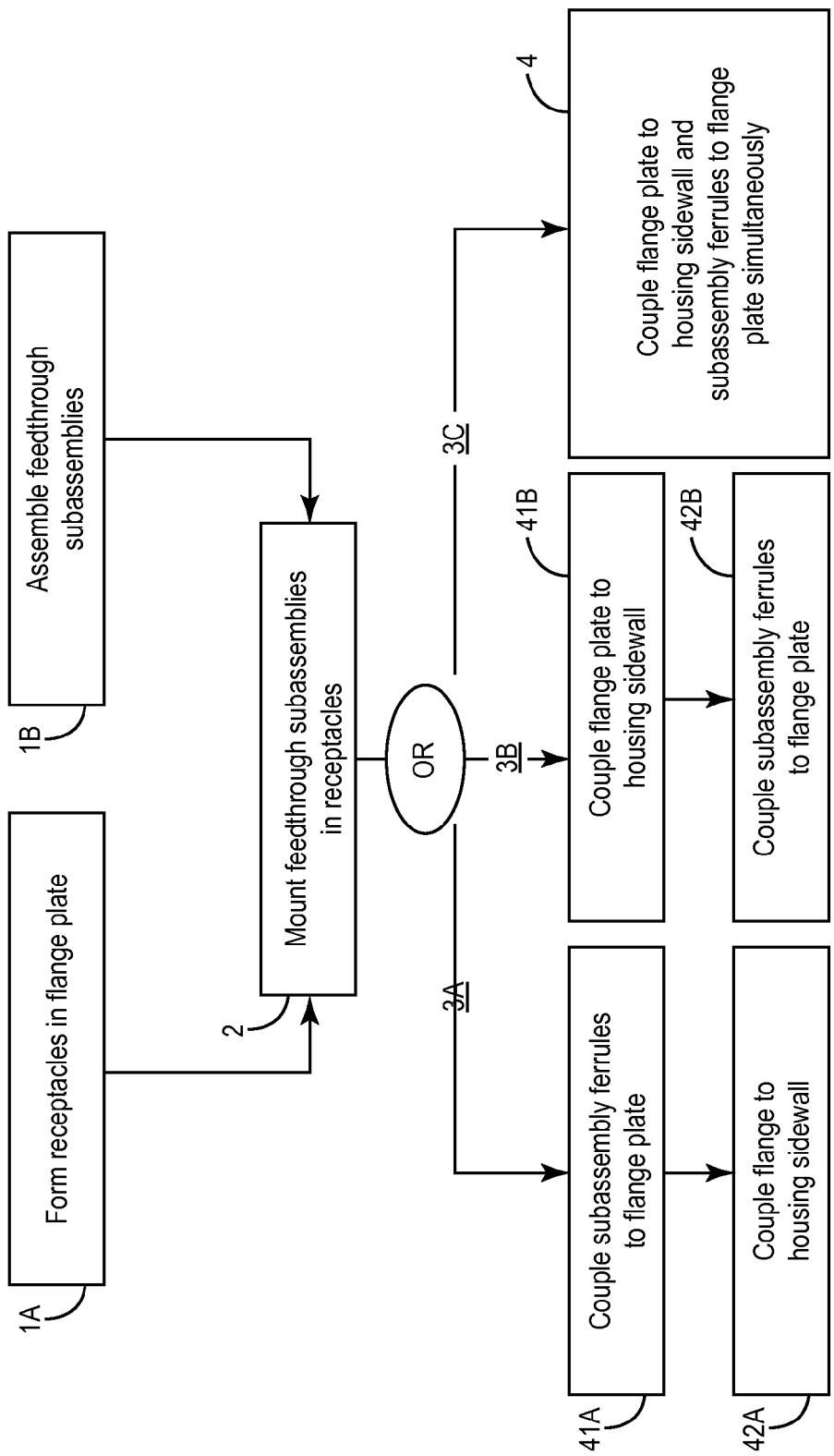
FIG. 4 is a flow chart outlining some methods of the present invention.

FIG. 4 is a flow chart outlining some methods of the present invention. According to steps 1A and 1B, a flange plate and corresponding feedthrough subassemblies may be manufactured independently and then brought together in step 2. Assembling the feedthrough subassemblies independent of the flange plate and independent of an IMD housing provides flexibility of manufacturing to produce more than one type of feedthrough for a particular IMD. Following step 2, one of three alternate routes 3A, 3B, or 3C may be taken after the subassemblies are mounted in the flange plate. According to route 3A, a ferrule of each subassembly is coupled to the flange plate (step 41A) first and then the flange plate is coupled to an IMD housing sidewall (step 42A). According to route 3B, the flange plate may be coupled to the IMD housing side wall (41B) prior to coupling each ferrule of the subassemblies to the flange plate (42B). According to route 3C, the flange plate is coupled to the housing simultaneous with coupling the subassemblies to the flange plate. A suitable coupling method for each route is laser welding, and considerations surrounding laser welding operations are well known to those skilled in the art. Although not shown in FIG. 4, it should be understood that, according to another method of the present invention, step 41B precedes step 2, so that step 2 comes between steps 41B and 42B.

In the foregoing detailed description, the invention has been described with reference to specific embodiments. However, it may be appreciated that various modifications and changes can be made without departing from the scope of the invention as set forth in the appended claims.

The invention claimed is:

1. A medical device feedthrough assembly, comprising:
a flat electrically conductive flange plate including a plurality of receptacles, wherein the flange plate is configured to be mounted to a housing of an implantable medical device;
a plurality of feedthrough subassemblies, each subassembly including:
an electrically conductive ferrule coupled to the flange plate, the ferrule being mounted within a corresponding receptacle of the plate;
a feedthrough pin extending though the ferrule; and
an insulator mounted within the ferrule, the insulator surrounding the feedthrough pin to isolate the feedthrough pin from the ferrule, the insulator being sealed to the ferrule, and the insulator being sealed to the feedthrough pin,
wherein a first subassembly of the plurality of subassemblies includes an electronic filtering element coupled to the feedthrough pin thereof and mounted between the feedthrough pin thereof and the ferrule thereof, and
wherein a second subassembly of the plurality of subassemblies includes no electronic filtering element coupled to the feedthrough pin thereof, and
wherein the first and second subassemblies are configured to connect to electrical components of a medical device with internal couplings; and
a conductive wall protruding from the flange plate, wherein the conductive wall is configured to extend over a length sufficient to span a gap between the flange plate and internal couplings of the filtered feedthrough pin of the second subassembly of the plurality of subassemblies and the unfiltered feedthrough pin subassembly of the plurality of subassemblies to shield the filtered feedthrough pin from the unfiltered feedthrough pin.

2. The feedthrough assembly of claim 1, wherein each receptacle of the plurality of receptacles includes a hole extending through the flange plate, and the ferrule of each subassembly extends through the hole of the corresponding receptacle.

3. The feedthrough assembly of claim 2, wherein:
each receptacle further includes a counterbore; and
the ferrule of each subassembly includes a shoulder extending laterally within the counterbore of the corresponding receptacle.

4. The feedthrough assembly of claim 2, further comprising weld joints securing the ferrule of each subassembly to the flange plate at the hole of the corresponding receptacle.

5. The feedthrough assembly of claim 1, wherein the flange plate further includes a lower side and a protrusion extending from the lower side, wherein the protrusion separates two of the plurality of feedthrough subassemblies.

6. The feedthrough assembly of claim 1, wherein:
the first subassembly includes a diameter greater than that of the second subassembly;
a first receptacle of the plurality of receptacles includes a hole through which the first subassembly extends; and
a second receptacle of the plurality of receptacles includes a hole through which the second subassembly extends, the hole of the first receptacle having a diameter larger than the hole of the second receptacle.

7. The feedthrough assembly of claim 1, further comprising:
a glass seal, the insulator of the first subassembly being sealed to the corresponding ferrule and feedthrough pin by the glass seal; and
a brazed seal, the insulator of the second subassembly being sealed to the corresponding ferrule and feedthrough pin by the brazed seal.

8. The feedthrough assembly of claim 1, wherein the flange plate includes a ledge extending about a perimeter of the flange plate, wherein the ledge is configured to butt up against a surface of the housing of the implantable medical device.

9. The feedthrough assembly of claim 1, further comprising a weld joint about a perimeter of the flange plate to secure the feedthrough assembly to the housing of the implantable medical device.

10. The feedthrough assembly of claim 1, wherein the electronic filtering element includes a discoidal capacitor.

11. The feedthrough assembly of claim 1, wherein the plurality of feedthrough subassemblies comprises a third subassembly that has the same design as the first subassembly.

12. An implantable medical device, comprising:
electrical components;
a housing holding the electrical components, the housing including a sidewall, the sidewall including an opening extending therethrough;
a feedthrough assembly disposed within the sidewall opening; and internal couplings connecting the feedthrough assembly to the electrical components, wherein the feedthrough assembly comprises:
an electrically conductive flange plate including a plurality of receptacles and a perimeter coupled to the housing sidewall,
a plurality of feedthrough subassemblies, each subassembly mounted within a corresponding receptacle of the flange plate and including:
an electrically conductive ferrule coupled to the flange plate,
a feedthrough pin extending through the ferrule, and
an insulator mounted within the ferrule, the insulator surrounding the feedthrough pin to isolate the feedthrough pin from the ferrule, the insulator being sealed to the ferrule, and the insulator being sealed to the feedthrough pin,
wherein a first subassembly of the plurality of subassemblies includes an electronic filtering element coupled to the feedthrough pin thereof and mounted between the feedthrough pin thereof and the ferrule thereof and
wherein a second subassembly of the plurality of subassemblies includes no electronic filtering element coupled to the feedthrough pin thereof, and
a conductive wall protruding from the flangeplate and extending over a length sufficient to span a gap between the flange plate and internal couplings of the filtered feedthrough pin of the second subassembly of the plurality of subassemblies and the unfiltered feedthrough pin subassembly of the plurality of subassemblies to shield the filtered feedthrough pin from the unfiltered feedthrough pin.

13. The device of claim 12, wherein:
   each receptacle of the plurality of receptacles includes a hole extending through the flange plate, through which the corresponding ferrule extends) and a counterbore; and
   each ferrule includes a shoulder extending laterally within the corresponding counterbore.

14. The device of claim 12, wherein the flange plate further includes a lower side disposed within the housing and a protrusion extending from the lower side.

15. The device of claim 14, wherein the protrusion grounds the flange plate within the housing.

16. The device of claim 14, wherein the protrusion extends between a first feedthrough subassembly of the plurality of feedthrough subassemblies and a second feedthrough subassembly of the plurality of feedthrough subassemblies to shield the first subassembly from the second subassembly.

17. The device of claim 12, wherein:
   the first feedthrough subassembly includes a diameter and the second feedthrough subassembly includes a diameter larger than that of the first subassembly;
   the receptacle corresponding to the first feedthrough subassembly includes a hole through which the first feedthrough subassembly extends; and
   the receptacle corresponding to the second feedthrough subassembly includes a hole through which the second feedthrough subassembly extends, the hole of the receptacle corresponding to the second feedthrough subassembly being larger than the hole of the receptacle corresponding to the first feedthrough subassembly.

18. The device of claim 12, further comprising:
   a glass seal, the insulator of the first feedthrough subassembly being sealed to corresponding ferrule and feedthrough pin by the glass seal; and
   a brazed seal, the insulator of the second feedthrough subassembly being sealed to the corresponding ferrule and feedthrough pin by the brazed seal.

19. The device of claim 12, further comprising an antenna, the feedthrough pin of the first subassembly being coupled to the antenna and conducts radio-frequency signals.

20. The device of claim 12, wherein in a third subassembly of the plurality of subassemblies the feedthrough pin of the third subassembly grounds to the ferrule of the third subassembly.

21. The implantable medical device of claim 12, further comprising a first weld joint about a perimeter of the flange plate to secure the feedthrough assembly to the housing of the implantable medical device in the opening extending through the sidewall.

22. The implantable medical device of claim 21, further comprising additional weld joints securing the ferrule of each subassembly to the flange plate at the corresponding receptacle.

23. The implantable medical device of claim 12, wherein the electronic filtering element includes a discoidal capacitor.

24. The implantable medical device of claim 12, wherein the plurality of feedthrough subassemblies comprises a third subassembly that has the same design as the first subassembly.

* * * * *

UNITED STATES PATENT AND TRADEMARK OFFICE
CERTIFICATE OF CORRECTION

PATENT NO. : 7,725,190 B2  Page 1 of 1
APPLICATION NO. : 11/343056
DATED : January 30, 2008
INVENTOR(S) : Rajesh V. Iyer and Shawn D. Knowles It is certified that error appears in the above-identified patent and that said Letters Patent is hereby corrected as shown below:

Column 17
Line 4, delete "ferrule extends)" and insert in place thereof -- ferrule extends, --.

Signed and Sealed this

Twenty-seventh Day of July, 2010

David J. Kappos
*Director of the United States Patent and Trademark Office*